US006854128B1

(12) United States Patent
Faulk

(10) Patent No.: US 6,854,128 B1
(45) Date of Patent: Feb. 15, 2005

(54) FACIAL SKIN PROTECTIVE ASSEMBLY

(76) Inventor: William Faulk, 1108 W. Valley Blvd. #6300, Alhambra, CA (US) 91803

( * ) Notice: Subject to any disclaimer, the term of this patent is extended or adjusted under 35 U.S.C. 154(b) by 133 days.

(21) Appl. No.: 10/376,373

(22) Filed: Feb. 26, 2003

(51) Int. Cl.[7] .............................. A42B 1/00; A61F 7/00
(52) U.S. Cl. ........................ 2/9; 2/171.2; 2/174; 2/206; 607/109
(58) Field of Search ................................ 2/206, 9, 174, 2/171.2; 602/17, 74; 604/303; 606/204.35; 607/109; 132/319

(56) References Cited

U.S. PATENT DOCUMENTS

| 495,265 | A | * | 4/1893 | Pinault | 604/303 |
|---|---|---|---|---|---|
| 1,480,780 | A | * | 1/1924 | Pauley | 607/109 |
| 1,677,049 | A | * | 7/1928 | Procter | 604/303 |
| 4,173,795 | A | * | 11/1979 | Lundin et al. | 2/9 |
| 4,847,921 | A | * | 7/1989 | Leutholt et al. | 2/206 |
| 5,335,371 | A | * | 8/1994 | Spessard | 2/9 |
| 5,396,881 | A | * | 3/1995 | Klein | 601/23 |
| 5,527,357 | A | * | 6/1996 | Springer, Jr. | 607/140 |
| 5,623,733 | A | * | 4/1997 | Kurimoto et al. | 2/206 |
| 5,961,479 | A | * | 10/1999 | Reeves et al. | 602/74 |
| 6,012,164 | A | * | 1/2000 | Deal, III | 2/9 |

* cited by examiner

Primary Examiner—Rodney M. Lindsey
(74) Attorney, Agent, or Firm—Roy, Kiesel, Keegan & DeNicola

(57) ABSTRACT

A facial skin protective assembly for reducing and/or eliminating pulling and pushing forces on the facial skin surfaces that occur while sleeping. The facial skin protective assembly includes a face shield cage structure, a number of securing straps attached to the face shield cage structure and being extendable about the sides and back of the user's head in a manner to comfortably but firmly hold the face shield cage structure in place while the user is sleeping, and, as an option, a number of heat/cool insert cushion cells.

1 Claim, 2 Drawing Sheets

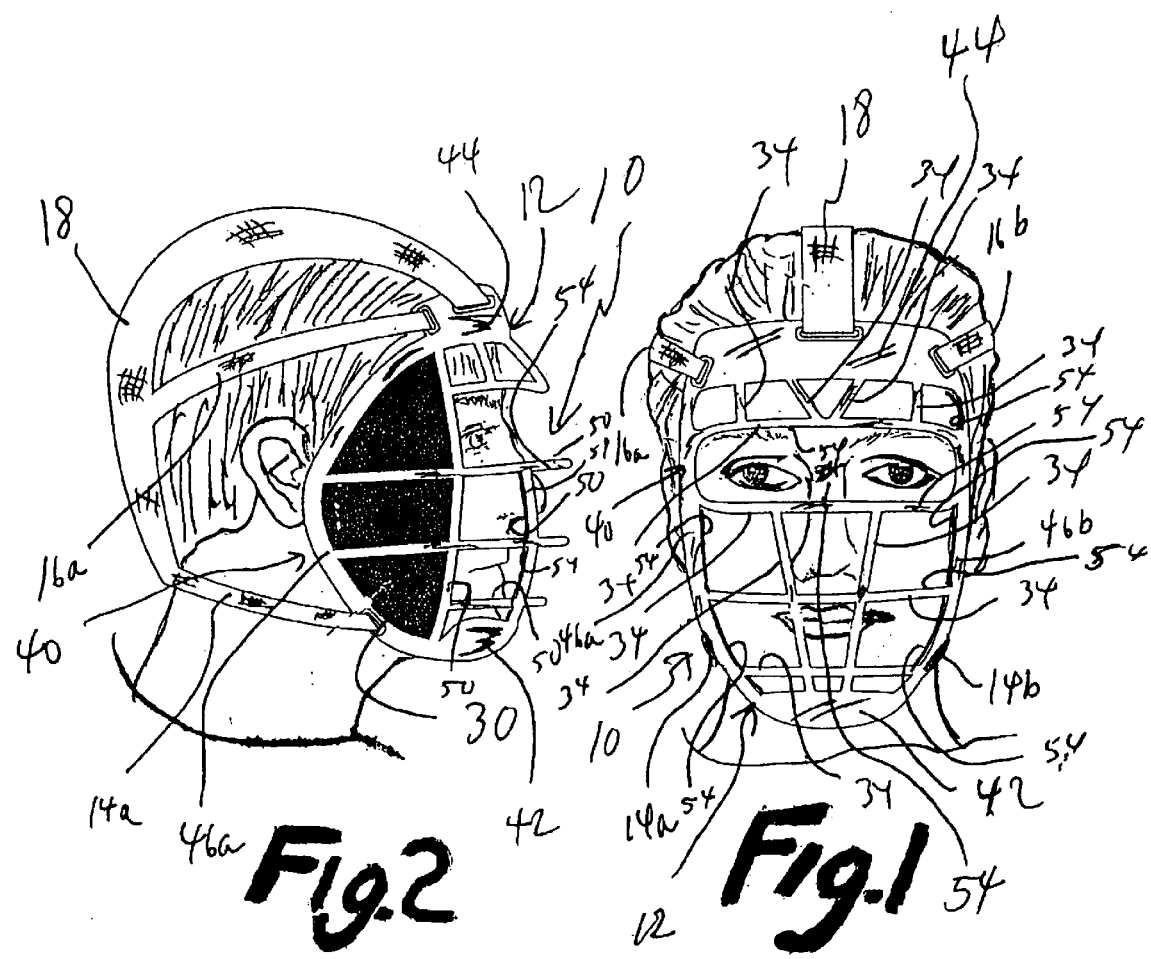

US 6,854,128 B1

FACIAL SKIN PROTECTIVE ASSEMBLY

TECHNICAL FIELD

The present invention relates to anti-aging devices and more particularly to a facial skin protective assembly that includes a face shield cage structure, a number of securing straps attached to the face shield cage structure that are extendable about the sides, top and back of the user's head in a manner to comfortably but firmly hold the face shield cage structure in place while the user is sleeping; and, as an option, one or more heat/cool insert cushion cells; the face shield cage structure being formed of a number of integrally formed, strategically positioned, rib members in connection with a cage surrounding structure including a jaw cup, a forehead plate and two curved side plates integrally formed in connection between the ends of the jaw cup and the forehead plate; the user facing surfaces of the face shield cage structure having gel-filled cushions on the face contacting surfaces; the optional one or more heat/cool insert cushion cells being positioned by a user at locations between the user's facial skin surface and open areas between the rib members of the face shield cage structure in a manner to reduce any pressure points caused by pillows or other sleeping equipment surfaces pulling or pushing on the facial skin as well as to provide an easy way for individuals to position hot or cold compresses in place where needed after having had facial or oral surgical procedures.

BACKGROUND ART

The facial skin is typically subjected to a variety of harmful pulling and pushing forces during a normal night of sleep. Over the years, the pressures and forces exerted on the facial skin can cause the facial skin to become wrinkled or form sag spots, such as below the eyes. It would of course be a benefit to a great many individuals to have a shield device that would minimize the pushing and pulling forces exerted on the facial skin during a normal sleep period so as to reduce their aging effects.

Because many individuals must place a compress, hot or cold, on a facial skin surface after having undergone a facial or oral surgery, it would be further benefit to have a shield device that was adapted to hold such compresses in place while the individual sleeps.

GENERAL SUMMARY DISCUSSION OF INVENTION

It is thus an object of the invention to provide facial skin protective assembly that includes a face shield cage structure, a number of securing straps attached to the face shield cage structure and being extendable about the sides and back of the user's head in a manner to comfortably but firmly hold the face shield cage structure in place while the user is sleeping, and, as an option, a number of heat/cool insert cushion cells; the face shield cage structure being formed of a number of integrally formed, strategically positioned, rib members in connection with a cage surrounding structure including a jaw cup, a forehead plate and two curved side plates integrally formed in connection between the ends of the jaw cup and the forehead plate; the user facing surfaces of the face shield cage structure having gel-filled cushions on the face contacting surfaces; the optional heat/cool insert cushion cells being positioned by a user at locations between the user's facial skin surface and open areas between the rib members of the face shield cage structure in a manner to reduce any pressure points caused by pillows or other sleeping equipment surfaces pulling or pushing on the facial skin as well as to provide an easy way for individuals to position hot or cold compresses in place where needed after having had facial or oral surgical procedures.

Accordingly, facial skin protective assembly is provided. The facial skin protective assembly includes a face shield cage structure, a number of securing straps attached to the face shield cage structure and being extendable about the sides and back of the user's head in a manner to comfortably but firmly hold the face shield cage structure in place while the user is sleeping, and, as an option, a number of heat/cool insert cushion cells; the face shield cage structure being formed of a number of integrally formed, strategically positioned, rib members in connection with a cage surrounding structure including a jaw cup, a forehead plate and two curved side plates integrally formed in connection between the ends of the jaw cup and the forehead plate; the user facing surfaces of the face shield cage structure having gel-filled cushions on the face contacting surfaces; the optional heat/cool insert cushion cells being positioned by a user at locations between the user's facial skin surface and open areas between the rib members of the face shield cage structure in a manner to reduce any pressure points caused by pillows or other sleeping equipment surfaces pulling or pushing on the facial skin as well as to provide an easy way for individuals to position hot or cold compresses in place where needed after having had facial or oral surgical procedures.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 1 is a front plan view of an exemplary embodiment of the facial skin protective assembly of the present invention secured over the facial region of a representative user.

FIG. 2 is a side plan view of the facial skin protective assembly of FIG. 1 secured over the facial region of a user, held in place by the securing straps positioned about the top, back and sides of the user's head and an optional heat/cool insert cushion cell positioned against the right side surface of the user's face by the face shield cage structure.

EXEMPLARY MODE FOR CARRYING OUT THE INVENTION

Figures 3, 4:
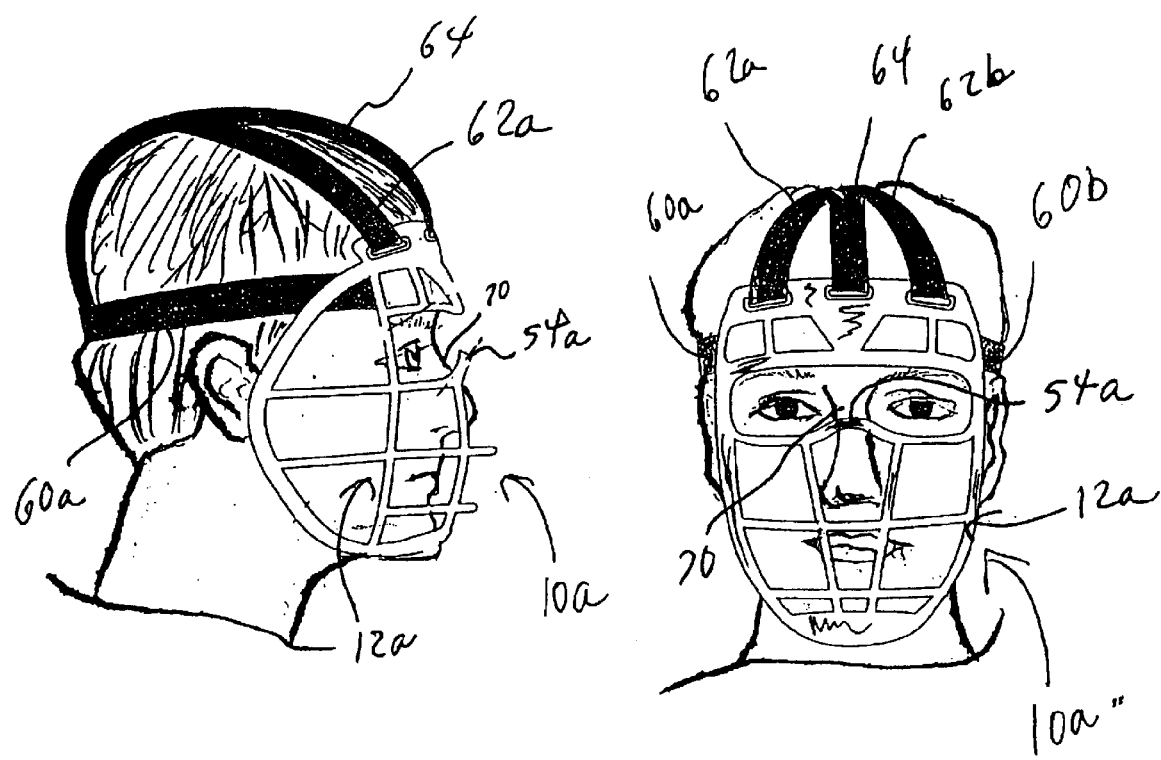
FIG. 3 is a front plan view of a second exemplary embodiment of the facial skin protective assembly of the present invention wherein the rib members of the face shield cage structure are configured differently from the embodiment of FIG. 1.
FIG. 4 is a side plan view of the facial skin protective assembly of FIG. 3 secured in place by the securing straps positioned about the top, back and sides of the user's head.

FIGS. 1–2 show various aspects of an exemplary embodiment of the facial skin protective assembly of the present invention generally designated 10. Facial skin protective assembly 10 includes a face shield cage structure, generally designated 12; a number of nylon securing straps 14a,14b, 16a,16b and 18 attached to the face shield cage structure 12 at the ends thereof and that are positionable about the neck, sides and top of the user's head in a manner to comfortably but firmly hold the face shield cage structure 12 in place while the user 26 is sleeping. In this embodiment, one heat/cool insert cushion cell 30 is provided for the optional use of the user when and where desired.

Face shield cage structure 12 is formed of a number of integrally formed, strategically positioned, rib members 34 in connection with a cage surrounding structure, generally designated 40, including a jaw cup 42, a forehead plate 44 and two curved side plates 46a,46b integrally formed in connection between the ends of the jaw cup 42 and the forehead plate 44. The user facing surfaces 50 of the face shield cage structure having gel-filled cushions 54 on the face contacting surfaces 50.

FIGS. 3 and 4 show a second exemplary embodiment of the facial skin protective assembly of the present invention, generally designated 10a that is substantially identical to facial skin protective assembly 10 except for a sightly different strap arrangement including two side straps 60a, 60b, two diagonal straps 62a,62b, and a top/back strap 64; and the downward and inward curved nose bridge rib 54a of face shield cage structure 12a rather than just the inwardly curved nose bridge rib 54 of face shield cage structure 12. The downward curve is added in this embodiment to provide more room between the bridge 70 of a user's nose and nose bridge rib 54a.

It can be seen from the preceding description that a facial skin protective assembly has been provided.

It is noted that the embodiment of the facial skin protective assembly described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A facial skin protective assembly comprising:

a face shield cage structure;

a number of securing straps attached to the face shield cage structure that are extendable about the sides, top and back of the user's head in a manner to comfortably but firmly hold the face shield cage structure in place while the user is sleeping; and a temperature controlling insert cushion cell;

the face shield cage structure being formed of a number of integrally formed, strategically positioned, rib members in connection with a cage surrounding structure including a jaw cup, a forehead plate and two curved side plates integrally formed in connection between the ends of the jaw cup and the forehead plate;

the user facing surfaces of the face shield cage structure having gel-filled cushions on the face contacting surfaces;

the temperature controlling insert cushion cell being positioned by a user at user selected locations between the user's facial skin surface and open areas between the rib members of the face shield cage structure in a manner to reduce any pressure points caused by pillows or other sleeping equipment surfaces pulling or pushing on the facial skin as well as to provide an easy way for individuals to position a temperature altering compress in a place where needed after having had facial or oral surgical procedures.

* * * * *